ized Patent [19]

Lares et al.

[54] DENTAL HANDPIECE

[76] Inventors: Joseph P. Lares, 111 Wellesley Crescent, Redwood City, Calif. 94062; Albert J. Lares, 351 Grove Dr., Portola Valley, Calif. 94025

[21] Appl. No.: 712,888

[22] Filed: Aug. 9, 1976

[51] Int. Cl.² ............................................. A61C 1/12
[52] U.S. Cl. ...................................... 32/27; 415/503
[58] Field of Search ............................ 32/27; 415/503

[56] References Cited

U.S. PATENT DOCUMENTS

| | | | |
|---|---|---|---|
| 621,036 | 3/1899 | Curry | 415/503 |
| 3,055,112 | 9/1962 | Borden | 415/503 |
| 3,092,908 | 6/1963 | Flatland | 32/27 |
| 3,228,657 | 1/1966 | Saffir | 32/27 |
| 3,298,103 | 1/1967 | Maurer | 32/27 |
| 3,408,043 | 10/1968 | Williams et al. | 32/27 |
| 3,411,210 | 11/1968 | Staunt | 32/27 |
| 3,499,223 | 3/1970 | Lieb et al. | 32/27 |
| 3,934,349 | 1/1976 | Eibofner | 32/27 |
| 3,947,966 | 4/1976 | Lieb et al. | 32/27 |
| 3,962,789 | 6/1976 | Flatland | 415/503 |

Primary Examiner—Russell R. Kinsey
Assistant Examiner—John J. Wilson
Attorney, Agent, or Firm—Lothrop & West

[57] ABSTRACT

A dental handpiece has a housing with a removable cap together defining a chamber in which are coaxially mounted two bearings, each with an inner race and an outer race spaced apart to leave an intervening gap. Annular housing shields extend into the gaps. The bearings are mounted in elastomeric rings, each having a circular-cylindrical mounting surface. A shaft is disposed in the inner races of the rings. Between the bearings the shaft carries a turbine runner including two cups each having a hub and having peripheral turbine blades spaced apart a predetermined distance. The cups are mounted on the shaft with the cups facing each other so that the hubs and peripheries abut in a common plane normal to the axis and also defining a central annular space. The turbine blades are staggered with respect to each other. They receive air from an inlet passage in the housing and release air to an outlet passage in the housing.

2 Claims, 3 Drawing Figures

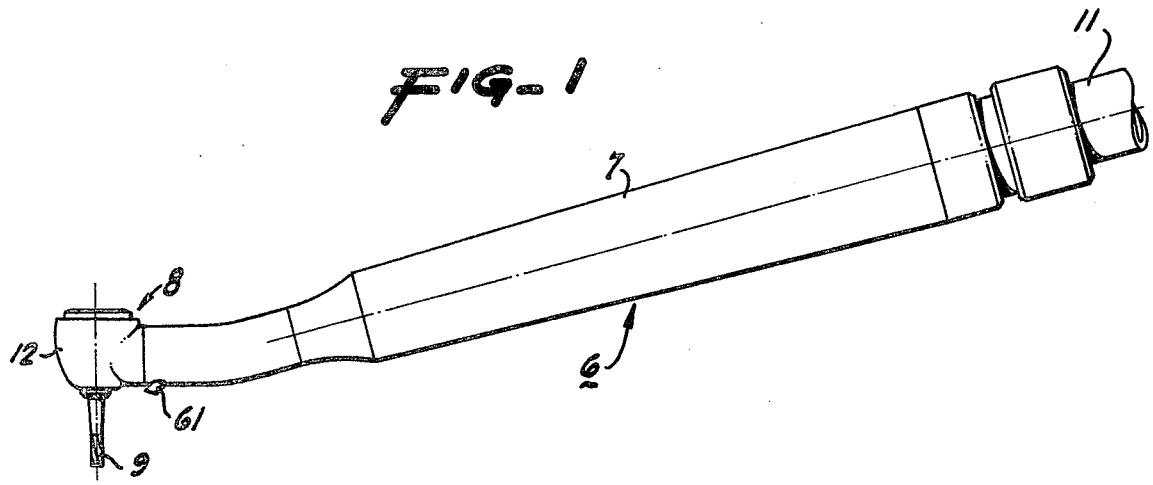
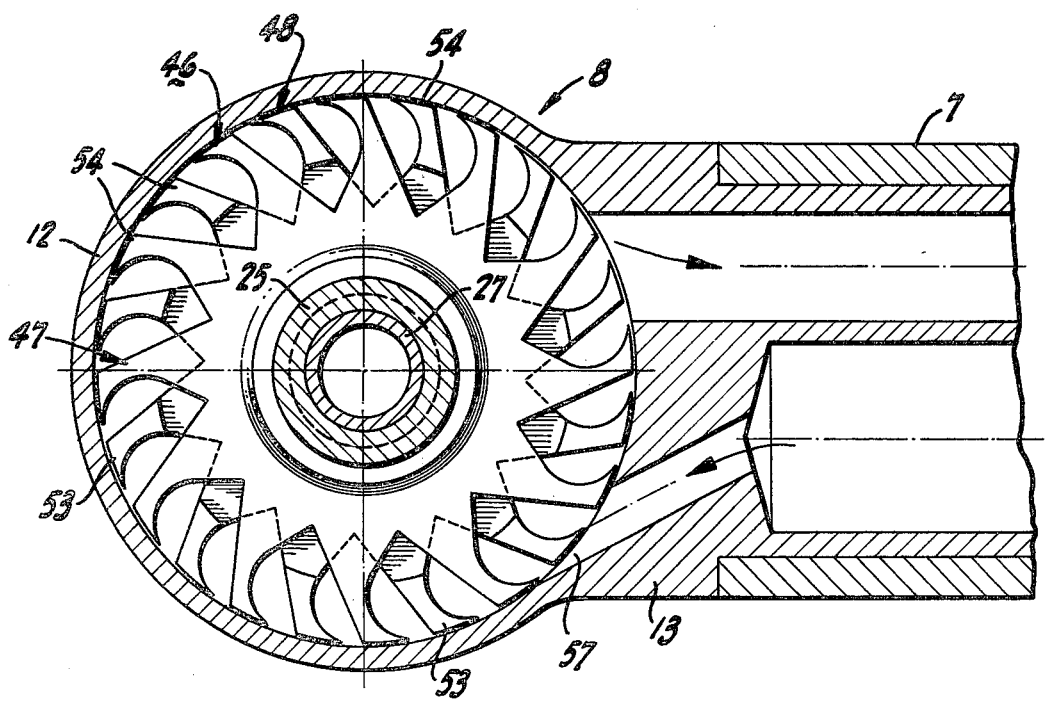

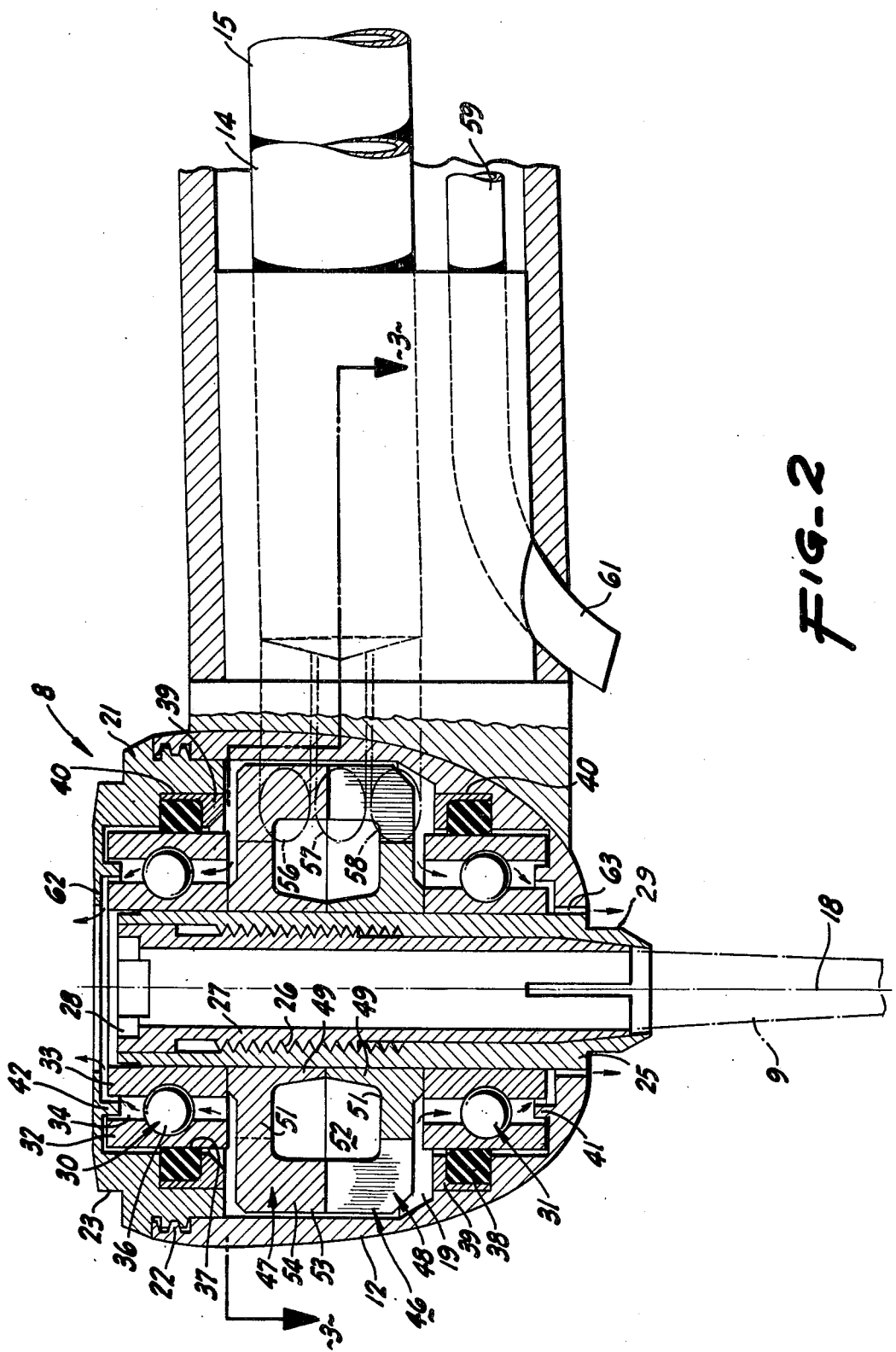

DENTAL HANDPIECE

BRIEF SUMMARY OF THE INVENTION

A dental handpiece includes a pair of oppositely facing, hollow cups having turbine blades around their peripheries arranged in a staggered relationship. Air comes toward the blades tangentially from an elongated air passage in a surrounding housing and flows against the blades, then into the hollow cups and then escapes through an air outlet from the housing. The cups are mounted on a shaft rotatable about an axis and carried in bearings having inner and outer races. The outer races are received in circular-cylindrical surfaces on non-rolling elastomeric mounting rings. The housing contains shields that extend into the spaces between the inner and outer races.

BRIEF DESCRIPTION OF THE SEVERAL VIEWS OF THE DRAWING

FIG. 1 is a side elevation of a dental handpiece constructed in accordance with the invention.

FIG. 2 is a cross-section on a longitudinal vertical plane through the handpiece of FIG. 1, illustrated to a greatly enlarged scale.

FIG. 3 is a cross-section, the planes of which are indicated by the lines 3—3 of FIG. 2.

DETAILED DESCRIPTION

A dental handpiece 6 includes the customary shank 7 for manipulation and a head 8 designed to drive a dental burr 9 or comparable tool by means of air under pressure from a suitable source 11.

The shank 7 is of a standard sort and is not disclosed in detail, but the head 8 includes a housing 12 merging with a sleeve 13 fitted into the end of the shank in any suitably firm fashion. The air supply 11 extends to an air inlet duct 14 within the sleeve 13. An air outlet duct 15 likewise is within the sleeve 13 and is carried out in any suitable way through the shank.

The housing 12 is inclusive of a main body symmetrical about an axis 18 and internally configured to define a chamber 19 symmetrical with the axis 18. A closure cap 21 engages the housing by a threaded interconnection 22 including a cylindrical pilot surface and a planar stop surface. There are flats 23 on the cap for a wrench.

Designed to be disposed within the housing symmetrically with the axis 18 is a tubular shaft 25 provided with internal threads 26 to carry a quill 27 for the reception of the dental tool 9 and in effect forming a chuck or collet therefor. The collet or chuck has a wrench-receiving end 28 thereon and the shaft 25 similarly has a wrench-receiving portion 29.

Situated between the housing cap and the tubular shaft 25 and similarly situated between the housing 12 and the tubular shaft 25 is a pair of high-speed antifriction bearings 30 and 31 respective. Since the bearings are similar, a description of one applies likewise to the other. Each bearing is inclusive of an outer race 32 and an inner race 33 separated to provide a gap 34 between races. Antifriction balls 36 operate within the races. The inner races are engaged with the tubular shaft 25.

In order to mount the bearings appropriately, the outer race of each of them is in immediate contact with a circular-cylindrical inner face 37 on an annular elastomeric ring 38. The ring is preferably thermally bonded to an L-shaped metal carrier 39 receivable in an annular groove 40 in the housing or in the cap. While the inner circular-cylindrical surface 37 can be provided by molding, it is also sometimes provided by a grinding operation. The elastomeric rings serve as appropriate mountings for the bearings to reduce and damp vibration and noise. The rings are especially provided with the circular-cylindrical abutting surface 37 so that upon assembly the elastomeric material does not roll or deform, but the rings simply slide into position with respect to the outer races 32 and remain in a uniform elastomeric condition without localized or specialized stresses. In this way the locations are accurate and any inevitable vibration is absorbed in an optimum fashion. Noise is transmitted as little as possible.

The gap 34 between the inner and outer races is in part occupied by an annular shield 41 in the body or housing and a comparable annular shield 42 in the cap so that there is no direct air flow path between the races. Rather, a devious path is provided.

Disposed on the shaft 25 between the inner races 33 of the two bearings and within the chamber 19 of the housing is a turbine runner 46. This is not a single structure but is comprised of a pair of cups 47 and 48 which are quite similar. Each of the cups has a central hub 49 offset from a radial web 51 thereon to leave a cavity 52. The web terminates in a peripheral flange 53 in which are cut at predetermined peripheral intervals a plurality of turbine blades 54 of a special configuration, concave on the trailing side of each turbine blade and forming a circumferential row of blades, as illustrated.

Since the cup peripheries and hubs terminate on planes transverse to the axis 18, the cups are assembled or abutted in a common plane facing in opposite directions between the bearings and polarly rotated each with respect to the other so that the turbine blades in the two rows are peripherally or circumferentially staggered, as shown particularly in FIG. 3.

To supply the turbine, the air passage 14 at its end near the housing 12 is divided into three mutually parallel air inlet passages 56, 57 and 58, all arranged with their axes in the same general plane tangent to the turbine runner and directed in a tangential direction toward concave, trailing sides of the turbine blades. Similarly, but in a less restricted fashion, the chamber 19 is connected directly to the air outlet duct 15.

If desired, alongside the inlet and outlet ducts in the shank there is a water tube 59 having an outlet 61 directed toward the dental tool 9.

In the operation of this device with the ducts in operation, air under pressure from the duct 14 is carried through the passages 56, 57 and 58 and emerges therefrom in a tangential direction onto the concave, trailing sides of the turbine blades. Since these blades are divided axially into two sets and are staggered peripherally or circumferentially, the number of individual impulses given to the rotor is twice as great as though all of the blades were in axial alignment. This changes the sound frequency of the rotor and affords a smoother average impulse drive. Further, the exhaust air, which has spent much of its force in impacting one or more of the turbine blades, departs readily therefrom by moving with an inward component into the interior or cavity 52 of the turbine wheel and then outwardly with some axial component between inactive blades away from the periphery of the turbine wheel, to escape through the air outlet conduit 15.

Some of the air can travel axially and radially between the inner and outer races of the bearings both above and below the turbine wheel, being somewhat baffled in escaping therefrom by the shields 41 and 42. This tortuous path reduces unwanted sonic effects while leaving the air free to escape to the atmosphere either through an opening 62 in the cap or through an annular opening 63 between the housing 12 and the shaft 25.

The rotating parts revolve at a relatively high rate, of the order of five hundred thousand revolutions per minute. Despite the relatively high speed, the rotor operates quite quietly and smoothly, partly because it is insulated from the surrounding housing by the elastomeric rings 38 and partly because it can find its own center both axially and radially due to deformation of a uniform character in the elastomeric rings. By reason of the arrangement of these parts and the mounting of the turbine, as well as the staggered nature of the turbine blades and the ample exhaust air passages provided in the vicinity of the turbine runner, and because of other factors such as the shield or baffles, there is afforded a dental handpiece capable of high-speed operation in a very quiet, smooth fashion.

We claim:

1. A dental handpiece comprising a housing, a pair of bearings in said housing disposed coaxially on an axis, a shaft mounted in said bearings coaxially on said axis, a turbine runner including a pair of rotors on said shaft, each rotor having a central hub at one end abutting a respective one of said bearings and at the other end abutting the hub of the other rotor in a common terminal plane, a pair of webs, each web extending adjacent said one end only from a respective one of said hubs in a direction normal to said axis and each of said webs having a plurality of circumferentially spaced blade portions around the periphery thereof and extending axially from each web only toward the other web and terminating in said common terminal plane, with said blade portions of one of said webs being peripherally staggered with respect to the blade portions of the other of said webs and being radially spaced from said hubs to leave a central annular space between said blades and hubs, means on the trailing side of each of said blade portions defining a concave impact surface extending the axial length of said blade and disposed to direct air into said central annular space, means providing a plurality of inlet passages in said housing substantially tangent to said blade portions and extending substantially the entire axial height of both of said rotors, and means providing an outlet passage in said housing for air issuing from said central annular space between said blade portions.

2. A dental handpiece as in claim 1 in which at least one of said bearings has an inner race and a surrounding outer race radially spaced from said inner race to leave an axially extending radial gap, and an annular shield on said housing extending axially at least partway into said gap and radially spaced from said inner race and said outer race.

* * * * *